(12) United States Patent
Adkins et al.

(10) Patent No.: US 6,480,638 B1
(45) Date of Patent: Nov. 12, 2002

(54) SINGLE MODE FIBER OPTIC EVANESCENT WAVE REFRACTOMETER

(75) Inventors: Charles M. Adkins, Charlottesville; David Gerdt, North Garden; Marin Baruch, Charlottesville, all of VA (US)

(73) Assignee: Empirical Technologies Corporation, Charlottesville, VA (US)

( * ) Notice: Subject to any disclaimer, the term of this patent is extended or adjusted under 35 U.S.C. 154(b) by 46 days.

(21) Appl. No.: 09/642,375

(22) Filed: Aug. 21, 2000

Related U.S. Application Data
(60) Provisional application No. 60/150,011, filed on Aug. 20, 1999.

(51) Int. Cl.[7] .................................................. G02B 6/00
(52) U.S. Cl. .............................. 385/12; 385/29; 385/30; 422/82.11
(58) Field of Search ............................. 385/12, 13, 30, 385/29; 422/82.11; 250/227.11

(56) References Cited

U.S. PATENT DOCUMENTS

| 4,752,132 A | * | 6/1988 | Pavlath ........................ 356/345 |
| 5,494,798 A | * | 2/1996 | Gerdt ............................. 435/6 |

* cited by examiner

Primary Examiner—Cassandra Spyrou
Assistant Examiner—Leo Boutsikaris
(74) Attorney, Agent, or Firm—Miles & Stockbridge P.C.

(57) ABSTRACT

The invention relates broadly to a fiber optic sensor device, advantageously, a refractive index measurement device. A light emitting member transmits light, preferably coherent light, to a light splitter. The light splitter splits the light into a first portion that is transmitted to a first fiber optic coupler having an input optical fiber member and an optical fiber member having a waist region. A first output optical fiber member emerges from the first fiber optic coupler waist region. The light splitter is positioned to insert light into the first fiber optic coupler input optical fiber member. A reference fiber optic coupler includes an input optical fiber member and an optical fiber member having a waist region. The reference fiber optic coupler is enclosed in a potting medium stable reference of constant refractive index. A reference output optical fiber member emerges from the reference fiber optic coupler waist region. The light splitter member inserts a second portion of the split light into the reference fiber optic coupler input optical fiber member. A sum difference device processes the measured light emitted from the first output optical fiber member and from the reference output optical fiber member whereby the value derived said measured light emitted from said first output optical fiber member is independent of variations in light from said light emitting member.

17 Claims, 7 Drawing Sheets

SINGLE MODE FIBER OPTIC EVANESCENT WAVE REFRACTOMETER

CROSS-REFERENCE TO RELATED PATENT APPLICATION

This application claims the benefit of copending provisional patent application Ser. No. 60/150,011, filed Aug. 20, 1999, Adkins and Gerdt, the disclosure of which is incorporated herein by reference, as thought recited in full.

BACKGROUND OF THE INVENTION

1. Field of the Invention

This invention is in the field of chemical and biological assay and is useful for measurement of variables which are addressable through sensitive measurements of the index of refraction.

2. Brief Description of the Prior Art

Evanescent wave spectroscopy is not new. It is a variant of internal reflection spectroscopy and many configurations are thoroughly described in a text by N. J. Harrick. The concept works generally through the illumination of an optical interface which is in contact with a sample material; interaction with the sample occurs through evanescent wave sampling. Some configurations operate near the angle of total internal reflection and the sample index is tested either by measurement of the critical angle or by measurement of light loss as the solution index changes. Additional methods are provided through measurement of evanescent wave adsorption. In bulk optical systems, the light intensity is low and suitable sensitivity is obtained by multiple exposures to the sample interface, usually by geometric constructions which provide multiple reflections.

Some multimode fiber optic variants to the theme are described in Harrick's book. They operate on the same principal as the bulk optic devices with extended exposure to the fiber/sample solution interface provided by the multi-bounce propagation method in the multimode fiber. Sensing is via intensity variation at the output.

Three construction variants, based on multimode optical fibers, have been proposed in the literature as candidates for immunoassay. In the first, the fiber cladding is stripped to expose the core, and antigens, labeled with fluorophores, are attached to the fiber surface. The fluorophores are excited by the evanescent field and can be detected through reduction in the light level of by collection of the fluorescence. A second type of fiber optic immunoassay sensor uses a coating deposited on the fiber tip that can be illuminated by an optical pulse, which in turn induces fluorescence which is reflected back up the fiber and detected. A third type of fiber optic sensor for immunoassay involves a stripped fiber core that has antibodies and antigens attached to the core/solution interface. This sensor is used as one leg of a fiber optic Mach-Zender interferometer. The binding of molecules to the surface during attachment of either antibody of antigen suffices to locally change the index of refraction at the core/solution interface. This changes the phase velocity of the light on one leg of the device and interference fringes are observed at its output.

Still other configurations of immunosensors have been described such as surface plasmon resonance immunosensors, and grating couplers, used as integrated optical chemical sensors. These and others are discussed in the book edited by Wolfbeis. Velander and Murphy at Virginia Tech have proposed a fiber optic technique for an immunoassay that uses a grating superimposed on the fiber to scatter light into the cladding where it can sample the cladding/air interface. An affinity aerogel coating is used to collect and concentrate target antigens which are measured through the absorption spectrum of the returned light. Still more methods based on evanescent field absorption in optical waveguides are described by G. Stewart.

Conventional evanescent wave spectrometry has been thoroughly researched and is well known in the literature. The techniques involved are also used in fiber optic sensing. The processes usually rely on absorption processes in regions of waveguides where the evanescent field penetrates the guide. The guides are arranged so that as many reflections as possible illuminate the sample interface. Even so, the places where ray optics allows interaction between the optical species and the sample arc comparatively few and the illumination is weak compared to the single mode fiber optic coupler approach.

In large multimode optical fibers, a relatively large number, possibly hundreds, of spatial modes are supported. The modes can and do interfere with each other leading to extensive noise generation at the point of detection (i.e. speckle). The detector can't distinguish between intensity variations due to the sample and intensity variations that occur due to random inference between the propagating optical modes.

In contrast, single mode fibers only support one propagating mode. Therefore random interference is impossible and no modal redistribution occurs due to environmental factors. Another significant advantage of single mode fibers is that more than 90% of the optical energy can be forced into the evanescent field and that field surrounds the entire space immediately surrounding the core.

Interferometric approaches are usually the most sensitive available, however they require exceptional mechanical stability. In the fiber optic case, the interferometric technique suffers because the optical signal rotates due to birefringence in the bent fiber and path stability becomes a phenomenal problem. The single mode fiber optic coupler sensor is also an interferometric device, of sorts. However, the two legs of the interferometer (the two propagating supermodes) are both contained within the device itself. Because of this, the device is self-referencing and the noise associated with path instability is completely avoided.

The technique used by Veander and Murphy requires a spectrophotometer to read. Even in miniature configuration, this is hardly a "point of care" device useful in field environments.

In a prior patent, Gerdt and Herr correctly described the significant benefits of the single mode fiber optic coupler sensor relative to current and prior art. The disclosure of the prior patent. U.S. Pat. No. 5,494,798, Gerdt and Herr, Feb. 27, 1996, is incorporated by reference herein, as though recited in full. To summarize, the benefits include: 1) the high illumination levels exposed to the sample interface and the high sensitivity which result; 2) the single mode field exposed to the sample and the low noise which results with the elimination of other interfering modal noise components in the measured signal; 3) a measurement which uses only the variation in propagation constant to sense the measurement and is inherently separable from the multitude of intensity noise sources which encumber the measurement; 4) a differential signal output which allows normalization of the measurement and isolation from other noise sources.

In their patent, Gerdt and Herr proposed a method for immunoassay using the single mode fiber optic coupler sensor in conjunction with a surface coating of specific monoclonal or polyclonal antibodies to detect small concentrations of target antigens.

Figure 1:
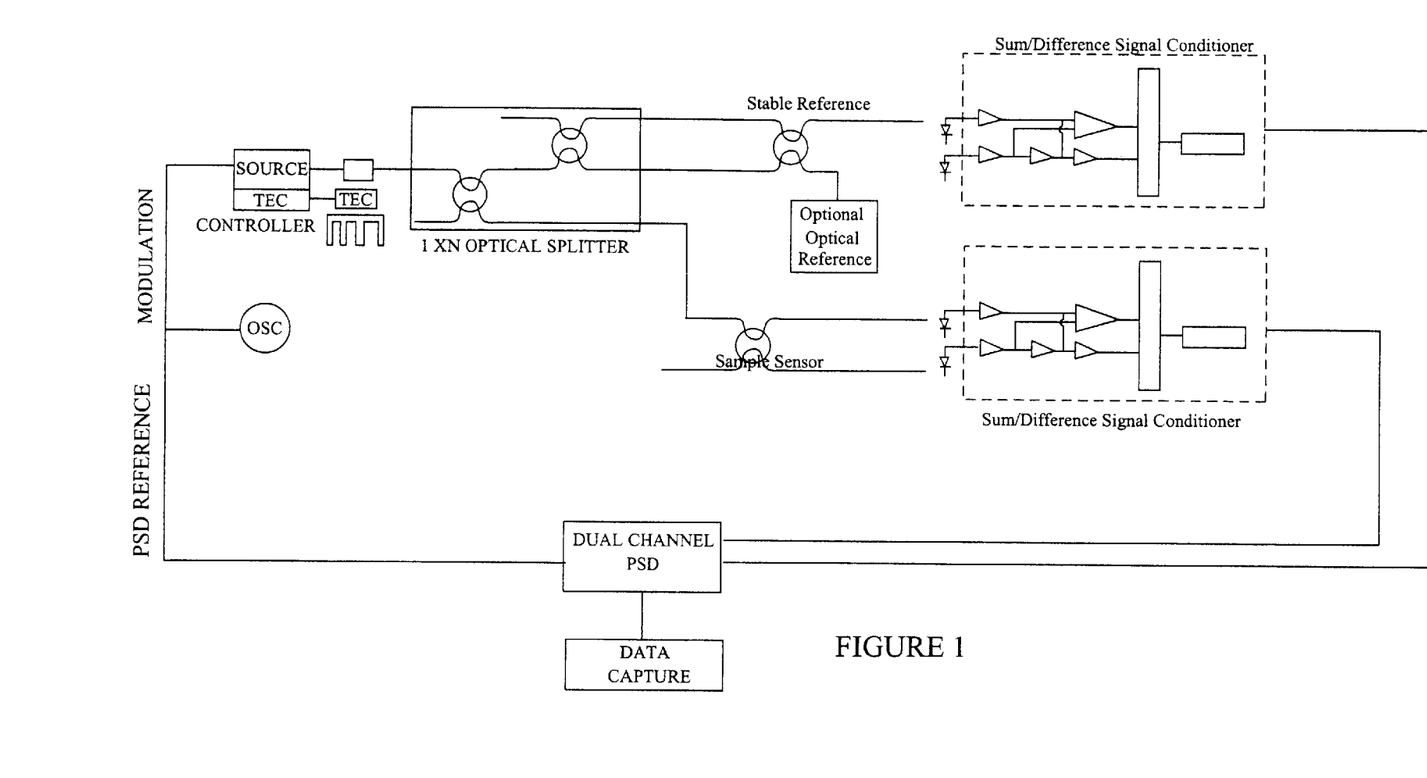
FIG. 1 is a schematic illustration of the system of the present invention.

There are three significant weaknesses in the method proposed which limit the ultimate sensitivity of the device and its use for quantitative measurement. The first occurs because the optical source produces noise components in both intensity and frequency. In their proposed method, the intensity noise is removed by conventional difference/sum signal processing of the optical output. Although the intensity noise components are removed by the method, the frequency noise components are enhanced along with the real signal. No method was provided to address this noise component that becomes significant at higher values of solution index of refraction. The second limitation occurs because the measured power splitting ratio is transcendental. Single measurements of the splitting ratio are not unique and no method is provided to quantitatively assess the solution index of refraction. The third limitation occurs because the gain and thus the noise figure in the initial detection stage is limited by the need to accept the full optical signal without clipping at large values of the coupling ratio which occurs periodically as the solution index is changed. As a result, small signal changes must be measured on a very large background. The signal, thus measured, is very small and system sensitivity suffers as the result. The proposed system, as illustrated in FIG. 1, includes a reference channel that addresses these shortcomings of the proposed method of the prior art.

SUMMARY OF THE INVENTION

The invention relates broadly to a fiber optic sensor device, advantageously, a refractive index measurement device. A light emitting member transmits light, preferably coherent light, to a light splitter. The light splitter splits the light into a first portion that is transmitted to a first fiber optic coupler having an input optical fiber member and an optical fiber member having a waist region. The coupler preferably is formed from a plurality of single mode fiber optic fibers. A first output optical fiber member emerges from the first fiber optic coupler waist region. The light splitter is positioned to insert light into the first fiber optic coupler input optical fiber member.

A reference fiber optic coupler includes an input optical fiber member and an optical fiber member having a waist region. The reference fiber optic coupler is enclosed in a potting medium stable reference of constant refractive index. A reference output optical fiber member emerges from the reference fiber optic coupler waist region. The first fiber optic coupler and the reference fiber optic coupler are single mode couplers.

The light splitter member inserts a second portion of the split light into the reference fiber optic coupler input optical fiber member.

A light measuring member is optically coupled to receive light emitted from the first output optical fiber member and the reference output optical fiber member. The light measuring member can be a light meter for measuring the magnitude of light.

A sum difference device processes the measured light emitted from the first output optical fiber member and from the reference output optical fiber member whereby the value derived said measured light emitted from said first output optical fiber member is independent of variations in light from said light emitting member.

The device of the present invention can be used for the immunoassay measurement of a target component. Light output from two or more of the sample coupler optic fibers are measured before and after surrounding the coupler with the target component. Light is measured from the reference coupler to establish a light reference value. The presence or concentration of the target component is determined by measuring changes in the output of light from the two or more optic fibers of the sample coupler due to the specific binding of the target component to the first immunoassay component as compared to the light reference value. The step of measuring changes in the output light preferably comprises a plurality of measurements made over a predetermine time interval and determining the rate of change of the light output. The step of comparing preferably includes comparing the rate of change of the light output as an indication of the concentration of the target material in the fluid.

The present invention advantageously includes an immunoassay method for determining a target analyte in a fluid sample. The method does not use labeled reagents and is based upon measuring changes in refractive index in an evanescent field surrounding a fiber optic coupler relative to light changes in a reference fiber optic coupler surrounded by a medium of stable refractive index. The method includes immobilizing an antibody or antigen capable of specifically binding to the target analyte on the fiber optic coupler and illuminating at least one of the plurality of optical fibers to provide the surrounding evanescent field with a first portion of light from a light splitter.

A first refractive index of the surrounding evanescent field is obtained by measuring a first ratio of light output by the fiber optic coupler. The fluid sample is brought into contact with the target fiber optic-coupler such that any target analyte in the fluid sample specifically binds to the immobilized antibody or antigen. A second refractive index of the surrounding field is obtained by measuring a second ratio of light output by the target fiber optic coupler.

The reference coupler is illuminated with a second portion of light from the light splitter to determine a illumination reference level by measuring light output from said reference coupler

DETAILED DESCRIPTION OF THE PREFERRED EMBODIMENTS OF THE INVENTION

A single mode optical fiber is comprised of three concentric components. The central component is called the core and is comprised of a material, usually quartz, with an index of refraction near 1.46. The core contains almost all of the propagating light and is sized just large enough to contain only one propagating mode, the fundamental. The core is surrounded by a concentric region called the cladding. The index of refraction of the cladding is slightly depressed relative to that of the core so that a guiding interface exists between the two regions. The cladding is of sufficient size that the propagating mode in the core is unaffected by variations in the environment which might surround the fiber. Quartz is susceptible to breakage if it is exposed to moisture, therefore the quartz components of the fiber are packaged in a third layer of a plastic material which provides a hermetic seal and protects the fiber during handling. This layer is called the buffer.

Figure 2:
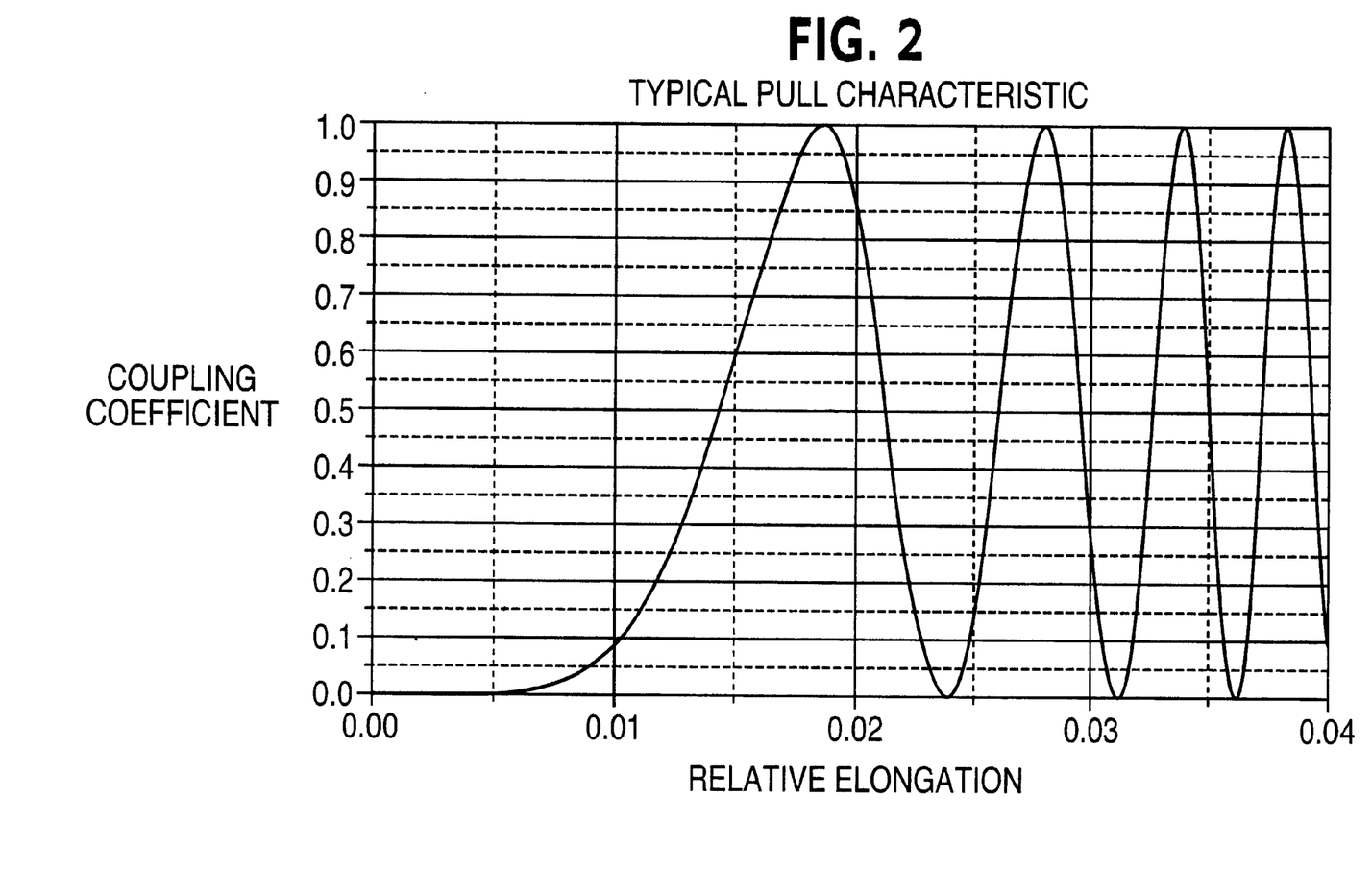
FIG. 2 is a graphic illustration of the variation in the coupling coefficient with elongation during the fabrication of the biconical fused tapered couplers.

If the plastic buffer is removed and two fibers are placed adjacent to each other in a furnace of flame, they will fuse. When the heated and fused fibers are gently pulled, they will elongate resulting in a reduction of both the fiber diameter and separation between the two cores. As this process continues, optical power in one of the fibers will begin to couple into the second fiber. As the fibers are pulled still further, the power will transfer completely to the second fiber and then begin to transfer back to the first fiber again, FIG. 2. This process will continue indefinitely, the light alternately transferring from one fiber to the other, until the fibers become too small and break.

Light, propagating in the cores of the two adjacent fibers, is described by the wave equation, a physical interpretation of Maxwell's equations applying to electromagnetic phenomena. The solution for this model is degenerate and results in two wave functions, one of which is symmetric and the other anti-symmetric relative to the geometric center of the pair of fibers. These wave functions are called the two "super modes". The propagating light at any point in the fibers is described by the vector sum of the two super modes and the optical power in each of the fibers is described by the square of their sum. The super modes extend beyond the fiber surface and into the surrounding material, however one of the modes extends a little further than the other and as a result, they propagate at different speeds. A phase difference, È, is accumulated between the super modes as they propagate over the fused length of the coupler. That phase difference depends on the length of the fused region, the wavelength of the illumination, and index of refraction of the core and cladding. The division of power between the two fibers is described by the coupling ratio, á, where:

$$á=Sin^2(É)$$

In the fused region of the coupler, the fiber diameter is reduced from an initial value near 125 microns to about 15 microns. The original core diameter is reduced in proportion. As the core is reduced, it can no longer contain the propagating mode and light spills into the surrounding cladding. After fabrication, almost all of the light resides in the original cladding material. The original cladding becomes the new core, and whatever surrounds the fused region, the sample solution, becomes the new cladding. As a result, the division of power between the two fibers becomes a strong function of the index of refraction in the small volume surrounding the fiber surfaces.

A mathematical model, which approximately describes the coupling ratio in terms of the fused length, the wavelength of the illumination, and the index of refraction of the core and cladding has been derived and published by J. Bures, S. Lacroix, and J. LaPierre, (1983). In their work, Bures, et. al. calculate the coupling ratio in terms of:

the wave number, $$k = \frac{2\pi}{\lambda}$$

the profile height parameter, $$\Delta = \frac{1}{2}\left(1 - \frac{n^2_{cladding}}{n^2_{core}}\right)$$

the waveguide parameter, $$V = kr(n_{core}^2 - n_{cladding}^2)$$

the core parameter, $$U = 2.405 e^{\frac{-(1+\Delta)}{V}}$$

and the cladding parameter, $$W = (V^2 - U^2)^{1/2}$$

then the coupling coefficient can be calculated $$C_{pp} = \frac{(2\Delta)^{\frac{1}{2}}}{r} \frac{U^2}{V^3} \frac{K_0(W*r)}{K_1^2(W)}$$

and the differential phase, calculated over the interval where $C_{pp}$ is non zero, is then $$\theta = \int C_{pp} \alpha l$$

the resulting coupling ratio is $$\alpha = Sin^2(\theta)$$

and the sensitivity is then defined as $$Sensitivity = \frac{\partial \theta}{\partial \lambda}\bigg|n = constant$$

In the preceding derivation, ë is the wavelength of the illumination, r is the ratio of core separation to the core radius, $n_{core}$ and $n_{cladding}$ are the indices of refraction of the core and cladding respectively. designates a partial derivative, and $K_0$ and $K_1$ are modified Bessel functions of the second kind.

Figure 3:
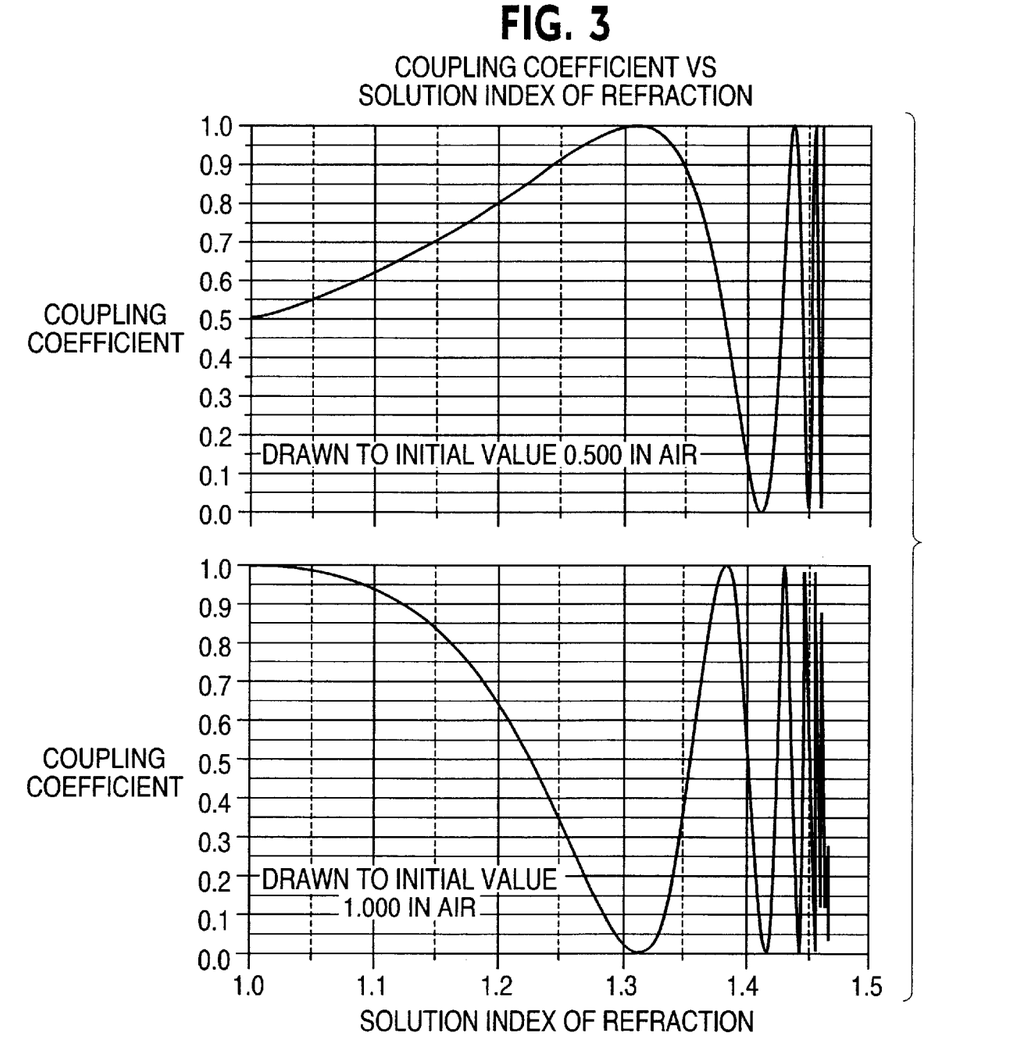
FIG. 3 is a graphic illustration of the variation in the coupling coefficient vs. solution index of refraction for biconical fused taper couplers drawn to different initial values in air.

FIG. 3, illustrates the variation of the coupling ratio, á, with solution index for couplers pulled to á=0.500 and 1.00 respectively, in air n=1.000. The figure demonstrates that the correlation between coupling ratio and solution index is not unique. A means is required to ratio.

Figure 4A:
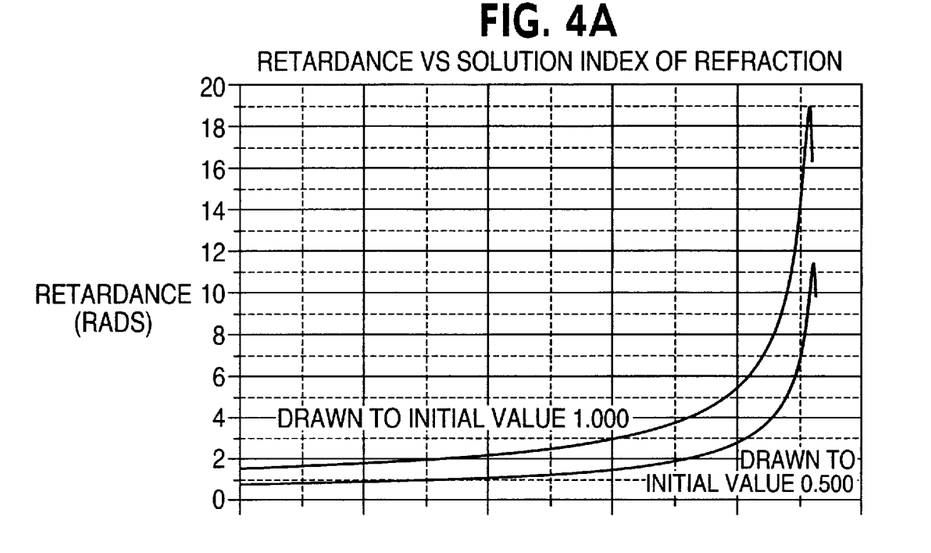
FIG. 4 is a graphic illustration of the variation in differential retardance and sensitivity vs. solution index of refraction for couplers drawn to different initial values in air.

FIG. 4a, illustrates the variation of the differential retardance, è, vs. the solution index for the same two couplers pulled to initial values of the coupling ratio, 0.500 and 1.00. Here, the measured function is monotonic, however, its measured value must be derived from the measurement of the coupling ratio, which is not. Since the retardance contains many cycles (N*2σ) it is still impossible to uniquely determine the index from the measured value.

Figure 4B:
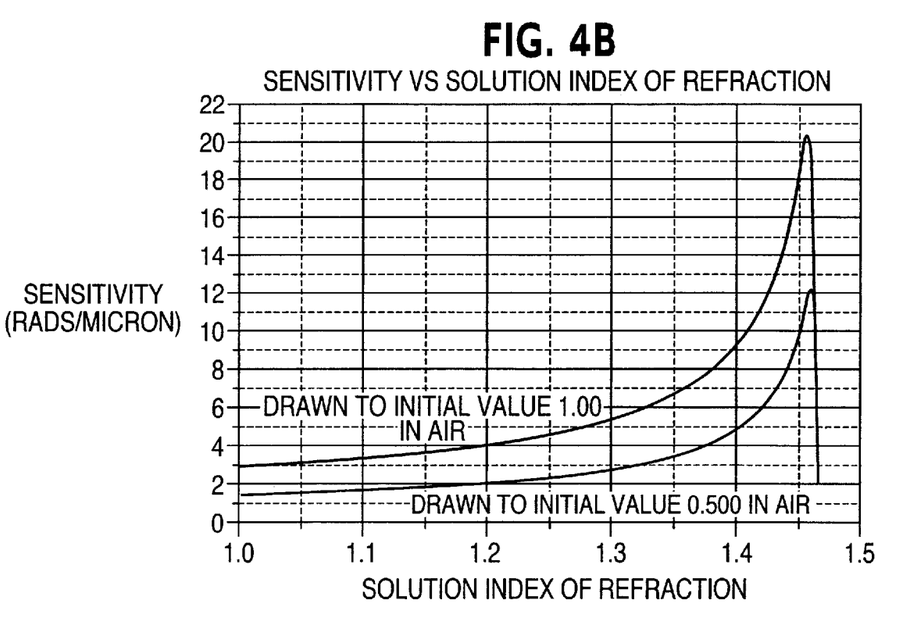

FIG. 4b, illustrates the first partial derivative of retardance relative to wavelength at constant index. This curve relates the signal change (retardance) that would result from changes in wavelength at constant values of solution index. If two couplers were simultaneously illuminated from the same source, the amount of change in signal (retardance) from the two couplers would depend on the index of refraction in each. If one of the couplers was immersed in a standard material of known index (the reference), the index of unknown sample could be uniquely and quantitatively determined by the ratio between the change in signal amplitude of the unknown and the change in signal amplitude of the reference. This ratio is uniquely defined for all values of index below the index of refraction of the coupler itself. At this value, dependent on the material in the optical fiber, the light becomes unguided and escapes. Measurements are not possible above this value.

Measurements, derived from the evanescent wave refractometer must be made from observation of the optical power in each of the fiber outputs and from calculations based on those observations. As has already been discussed, the total optical power in each coupler, $I_0$, is divided between its two output channels, $I_1$ and $I_2$. Remembering that the coupling ratio, $\acute{a}$, is the fraction of the total power in the coupler coupled into channel 2:

$$\alpha = \operatorname{Sin}^2(\theta)$$

then the power in the channels is $$I_1 = I_0(I - \operatorname{Sin}^2(\theta))$$

and $$I_2 = I_0 \operatorname{Sin}^2(\theta)$$

The coupling ratio, $\acute{a}$, and the retardance, $\grave{e}$, can be derived from measurements of the channel power levels, and calculated from the difference between the two channels, $\ddot{A}$, divided by the sum of the two channels, $\acute{O}$:

$$\frac{\Delta}{\Sigma} = \frac{I_0(\operatorname{Sin}^2(\theta)) - I_0(1 - \operatorname{Sin}^2(\theta))}{I_0(\operatorname{Sin}^2(\theta)) + I_0(1 - \operatorname{Sin}^2(\theta))}$$

from which it can be shown that the coupling ratio $$\alpha = 0.5\left(1 + \frac{\Delta}{\Sigma}\right)$$

and that $$\theta = A\sin(\alpha)^{1/2}$$

It is apparent that measurements of the coupling ratio of the retardance based on $\ddot{A}/\acute{O}$ are normalized to the instantaneous optical power and are, therefore immune to intensity noise in the source. From the previous derivation, however, it is also apparent that the measured values are still dependent on wavelength and that another means is required to remove that noise source. Inclusion of the second optical channel, the reference, potted in a material of constant index, provides that function.

Figure 5:
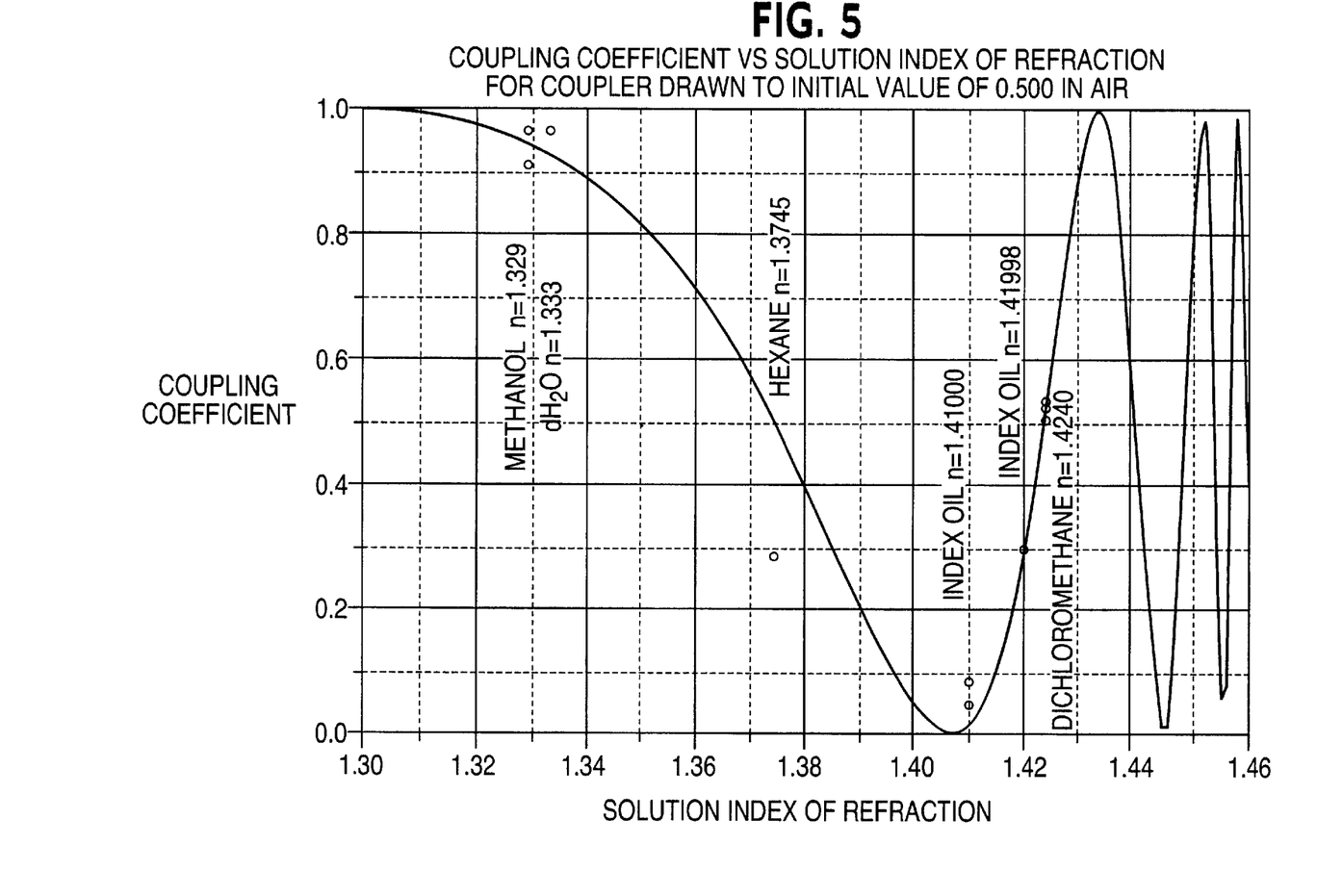
FIG. 5 is a graphic comparison of predicted values for coupling coefficient v. solution index of refraction and measured values for various solutions.
Figure 6:
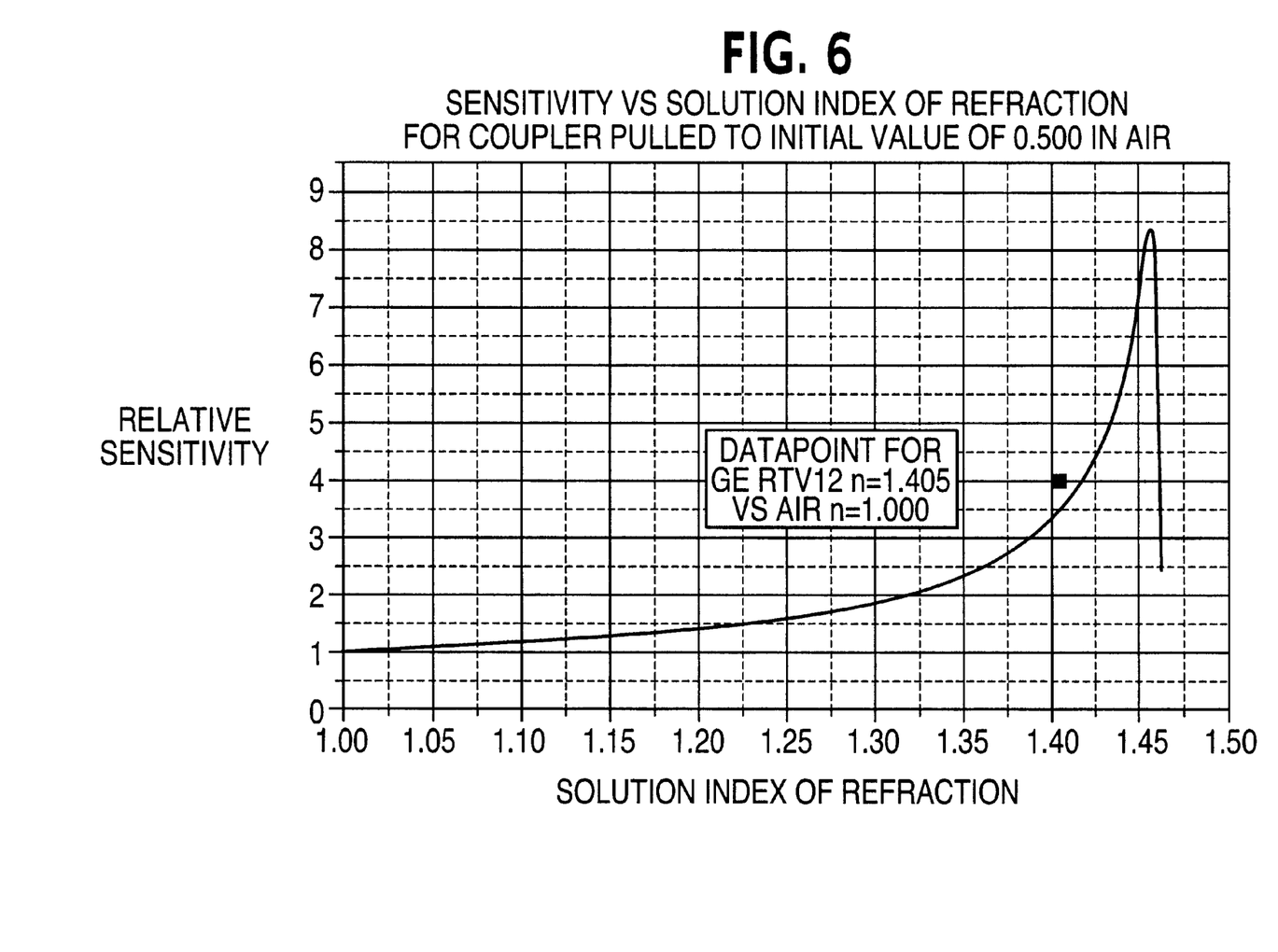
FIG. 6 is a graph of measured value for sensitivity for coupler pulled to initial value of 0.500 in air and potted vs. an identical coupler pulled to an initial value of 0.500 in air and unspotted.

Based on this model, predictions of the variation in coupling ratio vs. solution index of refraction for a coupler pulled to an initial value of $\acute{a}=0.5$ in air, $n=1.000$ is plotted in FIG. 5 and the ratio of signals obtained from a wavelength modulated source (relative sensitivity) for a coupler in air and a coupler in solutions of higher index is plotted as FIG. 6.

A preferred embodiment of the evanescent wave refractometer system is schematically described in FIG. 1. It is comprised of a pigtailed optical source (laser or light emitting diode) driven by a controller, a thermoelectric (Peltier) cooler and its thermoelectric controller, a splitter (a 1×N "tree" coupler with approximately equal outputs), a coupler used to measure the sample characteristics, a potted coupler used as a stable reference, detectors and transimpedance amplifiers for each channel of optical output and sum/difference processing for the sample and reference channels. An oscillator that also provides a reference signal for the dual channel Phase Sensitive Detector modulates the source controller. A plotter, logger, scope, or other display apparatus is used to capture the measurement output.

A less complicated version of the system is currently in use. In this system, output from the transimpedance amplifiers on each of the optical channels are independently collected by the data logger and data analysis is performed "off line" by computer based analysis packages. Using the lesser embodiment, a test system was constructed using a sample coupler drawn to an initial value of $\acute{a}=0.5$ in air and a stable reference whose initial value of $\acute{a}=0.5$ in GE RTV12, $n=1.420$, at the optical wavelength of 1.300 im. Data was collected at d.c. for the coupling coefficient obtained using several materials of known index. These measurements are plotted on FIG. 5 to illustrate the agreement obtained from the uncorrected measurement. The value obtained using Hexane, $n=1.3745$, shows significant error because Hexane rapidly attacks the tygon tubing used to construct the test apparatus.

Figure 7:
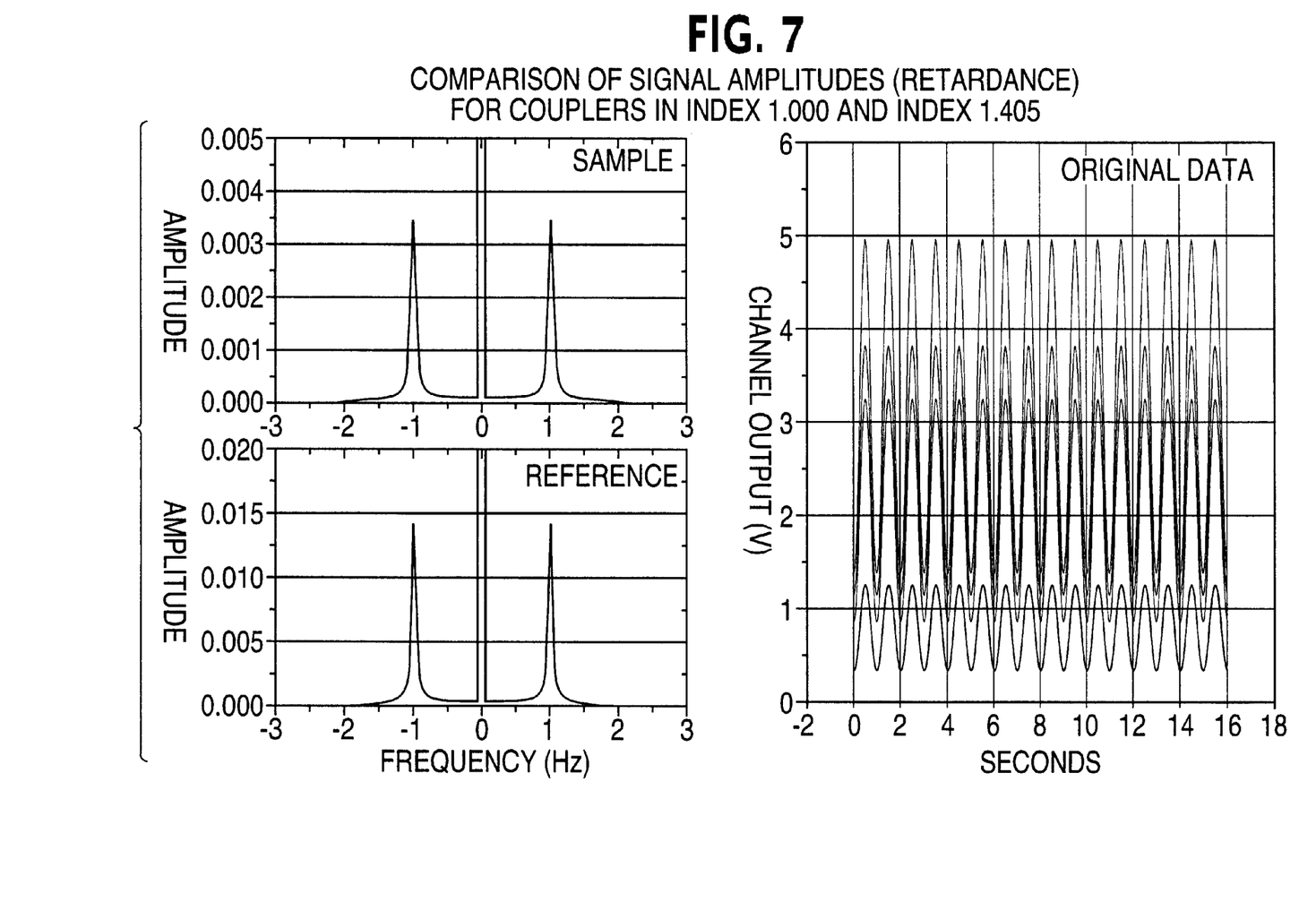
FIG. 7 are graphs of FFT's of calculated values for sinusoidal variation in coupling coefficient as the optical source wavelength is modulated.

The optical source was modulated at 1 Hz and the channel output data on FIG. 7 was collected for a sample coupler in air, $n=1.000$, and a reference coupler potted in GE RTV12, $n=1.402$. Instantaneous values of retardance were calculated and the variation in amplitude at the fundamental modulation frequency was derived from it using the Fast Fourrier Transform method. The ratio of signal amplitudes for that measurement is plotted on FIG. 6 to illustrate the accuracy of the method. The ratio of modulation signal amplitudes for the sample and reference predict the index of refraction for the sample without the uncertainty produced by using the coupling coefficient by itself.

OVERVIEW

A single mode fiber optic system has been constructed for quantitative measurement of chemical and biological reaction variables which are available through direct measurement of the solution index of refraction. Such variables include measurement of reaction extent and reaction kinetics through measurement of the solution index of refraction which is dependent on concentrations of the products and reactants. Further, through application of selected components to the sensing surface, concentrations of specific target components can be quantitatively measured with the extremely high sensitivity required for use in immunoassay.

The system is based on the fundamental properties of a biconical, fused tapered coupler as described by Gerdt. As a pair of single mode optical fibers are fused and drawn, optical power in the first fiber of the pair will couple into the second fiber of the pair. This division of power in the fibers is reflected in the coupling ratio (i.e. the coupled power as a percentage of the total power in the pair of fibers.) The coupling ratio is dependent on the degree of elongation in the fusion zone, the separation of the fiber cores, the wavelength of the illumination, and the index of refraction in the environment surrounding the fused and elongated portion of the fiber (i.e. the waist). If a coupler is drawn to and Initial Value (IV) of the coupling ratio in air and fixtured in a stable housing, any further change in power division is a function of the wavelength and the index of refraction in the sensing region.

Sensitivity and repeatability of the system are limited by system noise. The principal noise source in the system is the optical source, typically a solid state laser or light emitting diode. The noise is low frequency and demonstrates a 1/f characteristic which is well documented in the literature. A feature of the noise is that it contains components in both the amplitude domain (intensity noise) and n the frequency domain (frequency noise). The evanescent wave sensor as described by Gerdt, et. al. provides means to remove the intensity noise component through application of a well known difference/sum technique to the differential outputs of the sensor. It, however, amplifies the frequency noise component which appears in the measurement of the coupling ratio which the fundamental output of the device. The proposed system provides additional means to remove the frequency noise component in the output by comparison of the measured coupling ratio of the sample sensor with that of a stable reference, simultaneously illuminated by the optical source. The stable reference is an additional coupler which has been potted in a material of known index. Its output signal, also sampled through the same difference/sum technique, varies only with the wavelength of the source and allows the frequency noise component to be'subtracted from the measurement, thus eliminating optical system noise components to the limits of the detection apparatus.

The output from the evanescent wave sensor as described by Gerdt, et. al. is measured in terms of the coupling ratio. This ratio is transcendental and repeats the same value at multiple values of the sample solution index of refraction. Thus the measurement of a single value of the coupling ratio cannot be uniquely correlated to a value of solution index if the measurement is not continuous (e.g. if there is a rapid change or if the measurement is lost during intermediate steps in a chemical process). The inclusion of the stable reference in the measurement system allows quantitative evaluation of the sample index of refraction as a simple ratio of the variation in the signal from the sample sensor vs. the simultaneous signal variation from the stable reference as the source wavelength is changed.

If the frequency of the optical source is modulated (e.g. by intensity modulation of the laser or light emitting diode) then and a/c technique of measurement is obtained by which the index of refraction in the sample can be continuously and unambiguously measured as the ratio of signal levels in the sample channels relative to the signal levels in the stable reference.

Additionally, the a/c technique allows the use of the homodyne detection scheme which moves the sampling measurement out of the high noise environment at low frequencies and provides means for substantial signal/noise improvement through application of phase sensitive demodulation to the much larger signal levels which become available.

What is claimed is:

1. A fiber optic sensor comprising:
   a light emitting member;
   a light splitter member, said light emitting member being positioned to insert light into said light splitter member;
   a first fiber optic coupler having an input optical fiber member and an optical fiber member having a waist region;
   a first output optical fiber member emerging from said first fiber optic coupler waist region, said light splitter member being positioned to insert light into said first fiber optic coupler input optical fiber member;
   a reference fiber optic coupler having an input optical fiber member and an optical fiber member having waist region, said reference fiber optic coupler being enclosed in a potting medium;
   a reference output optical fiber member emerging from said reference fiber optic coupler waist region, said light splitter member being positioned to insert light into said reference fiber optic coupler input optical fiber member;
   a light measuring member optically coupled to receive light emitted from said first output optical fiber member and said reference output optical fiber member; and
   sum difference means for processing the measured light emitted from said first output optical fiber member and from said reference output optical fiber member whereby the value derived from said measured light emitted from said first output optical fiber member is independent of variations in light from said light emitting member.

2. The fiber optic sensor in accordance with claim 1 wherein said potting medium is a stable reference of constant refractive index.

3. The fiber optic sensor in accordance with claim 1 wherein said first fiber optic coupler and said reference fiber optic coupler are single mode couplers.

4. The fiber optic sensor in accordance with claim 3 wherein said first fiber optic coupler and said reference fiber optic coupler are each formed from a plurality of single mode fiber optic fibers.

5. The fiber optic sensor in accordance with claim 1 wherein said light inserted into said light splitter member is coherent light.

6. The fiber optic sensor in accordance with claim 1 wherein said light measuring member is a light meter for measuring the magnitude of light.

7. The fiber optic sensor in accordance with claim 1 wherein said potting medium is a stable reference of constant refractive index, said first fiber optic coupler and said reference fiber optic coupler are single mode couplers, and said first fiber optic coupler and said reference fiber optic coupler are each formed from a plurality of single mode fiber optic fibers, said light inserted into said light splitter member is coherent light, and said light measuring member is a light meter for measuring the magnitude of light.

8. A refractive index measurement device comprising in combination:
   a sample fiber optic coupler having a sample fusion joint;
   a reference fiber optic coupler having a reference fusion joint;
   a light splitter;
   a light input member positioned to input light into said light splitter;
   said light splitter inputting a first predetermined portion of said light into said sample fiber optic coupler, whereby an evanescent field is produced surrounding said sample fusion joint, and
   a second predetermined portion of said light into said reference fiber optic coupler;
   a light detector member for detecting light output from said sample fiber optic coupler and from said reference fiber optic couplery;
   a difference determination member for processing the detected light from said sample fiber optic coupler and from said reference fiber optic coupler;
   whereby the value derived from said detected light from said sample fiber optic coupler is independent of variations in light from said light input member.

9. The refractive index measurement device in accordance with claim 8, wherein said fusion joints are single mode couplers.

10. The refractive index measurement device in accordance with claim 9, wherein said coupler fusion joints are formed from a plurality of single mode fiber optic fibers.

11. The refractive index measurement device in accordance with claim 8, wherein said reference coupler is potted in a stable reference medium of constant refractive index.

12. The refractive index measurement device in accordance with claim 8, said light inserted into said light splitter is coherent light.

13. The refractive index measurement device in accordance with claim 8, wherein said light detector member is a light meter for measuring the magnitude of light.

14. A method of immunoassay measurement of a target component comprising the steps of:
- forming a sample coupler fusion joint from a plurality of single mode fiber-optic fibers;
- forming a reference coupler fusion joint from at least one single mode fiber optic fiber;
- coating the fusion-joint of said sample coupler with a first immunoassay component for specifically binding to the target component;
- surrounding the coated fusion joint with the target component;
- inserting light into a light splitter;
- transmitting light from a first split portion of light from said light splitter into one of said sample coupler optic fibers after coating the, fusion joint;
- transmitting light from a second split portion of light from said light splitter into said reference coupler at least one optic fiber;
- measuring light output from two or more of the sample coupler optic fibers before and after surrounding the fusion joint with the target component;
- measuring light from one or more of said reference coupler at least one optic fiber and establishing a light reference value;
- determining the presence or concentration of the target component by measuring changes in the output of light from said two or more sampler coupler optic fibers due to the specific binding of the target component to the first immunoassay component as compared to said light reference value.

15. A method of assay measurement of a target component in a fluid, using a device having
- a target single mode fiber optic coupler, said coupler having a fusion joint of at least two single mode optical fibers;
- a light splitter, and
- a reference single mode fiber optic coupler, said coupler having a fusion joint of at least one single mode optical fiber, which fusion joint is in a medium of stable index of refraction;

said method comprising the steps of:
- surrounding the fusion joint of said target optic coupler with the target component;
- inserting light into said light splitter;
- inserting light from said light splitter into one of said target coupler optical fibers;
- inserting light from said light splitter into said reference coupler at least one optical fiber;
- measuring and summing the output of light from two or more of the target coupler optical fibers and from said reference coupler at least one optical fiber, before and after surrounding the target coupler with the target component; and
- determining the presence or concentration of the target component in the fluid by comparing changes in the light output levels of said two or more optical fibers due to the target component relative to said, reference coupler light output levels.

16. The method of measurement in accordance with claim 15 wherein said step of measuring and summing comprises a plurality of measurements made over a predetermined time interval and further determining the rate of change of the light output and said step of comparing comprises comparing the rate of change of the light output as an indication of the concentration of the target material in the fluid.

17. An immunoassay method for determining a target analyte in a fluid sample, which method does not use labeled reagents and is based upon measuring changes in refractive index in an evanescent field surrounding a fiber optic coupler, said coupler having a plurality of optical fibers which are first coupled and then drawn to a single mode diameter, comprising:
- immobilizing an antibody or antigen for specifically binding to the target analyte on the fiber optic coupler;
- illuminating at least one of the plurality of optical fibers to provide the surrounding evanescent field with a first portion of light from a light splitter;
- obtaining a first refractive index of the surrounding evanescent field by measuring a first ratio of coupled power as a percentage of the total power in the optical fibers of the fiber optic coupler;
- contacting the fluid sample to the fiber optic coupler such that any target analyte in the fluid sample specifically binds to the immobilized antibody or antigen;
- obtaining a second refractive index of the surrounding field by measuring a second ratio of coupled power as a percentage of the total power in the optical fibers of the fiber optic coupler being in contact with the fluid sample; and
- illuminating at least one optical fiber of a reference coupler with a second portion of light from a light splitter, said reference coupler having at least one optical fiber that is drawn to a single mode diameter, said reference coupler being within a medium of stable refractive index, thereby determining an illumination reference level by measuring light output from said reference coupler.

* * * * *